United States Patent [19]
Weder et al.

[11] Patent Number: 5,997,888
[45] Date of Patent: Dec. 7, 1999

[54] COSMETIC PREPARATIONS

[75] Inventors: Hans Georg Weder; Marc Antoine Weder, both of Rüschlikon, Switzerland

[73] Assignee: Vesifact AG, Baar, Switzerland

[21] Appl. No.: 08/989,763

[22] Filed: Dec. 12, 1997

[30] Foreign Application Priority Data

Dec. 13, 1996 [CH] Switzerland .............................. 306596

[51] Int. Cl.$^6$ ..................................................... A61K 7/00
[52] U.S. Cl. ............................ 424/401; 514/78; 514/844; 514/846; 514/847; 514/848; 514/937; 514/938
[58] Field of Search .............................. 514/78, 844, 846, 514/847, 848, 873, 937, 938; 424/401

[56] References Cited

U.S. PATENT DOCUMENTS 5,733,572   3/1998   Unger et al. ............................. 424/450

FOREIGN PATENT DOCUMENTS

96/37192   11/1996   WIPO .

*Primary Examiner*—S. Mark Clardy
*Assistant Examiner*—Michael A. Williamson
*Attorney, Agent, or Firm*—Shoemaker and Mattare, Ltd.

[57] ABSTRACT

The cosmetic preparation contains: (a) an oil-soluble active ingredient that is suitable for skin cosmetics, (b) a partial fatty acid ester of polyoxyethylene sorbitan, (c) at least one phospholipid, (d) ethanol, and (e) water as a carrier liquid. The phospholipid is dissolved in ethanol, and then the partial fatty acid esters of polyoxyethylene sorbitan and the active ingredient are added. The oil phase that is obtained is added to water and stirred. The preparation is obtained in the form of a nanodispersion.

9 Claims, No Drawings

COSMETIC PREPARATIONS

BACKGROUND OF THE INVENTION

The subjects of this invention are cosmetic preparations based on nanodispersions and processes for their production.

Cosmetic preparations for skin care and for skin protection come in many forms of preparation, such as creams, ointments, pastes, gels, lotions, foams, sprays, etc. In addition to their aesthetic uses, such dermal cosmetic preparations also have several advantages that can be justified on therapeutic grounds. Owing to their adhesion to the epidermis and their penetrating power, these preparations are helpful mainly when they compensate for the loss of fat and moisture from the skin because of washing, weather and environmental influences, etc. and protect the epidermis from drying out. As so-called sunblocks, cosmetic preparations are especially important for counteracting the effects of UV rays from sunlight.

For cosmetic preparations, only active ingredients and additives that are soluble in the formulation base or are at least adequately solubilized are suitable. Moreover, they must be compatible with the other adjuvants in the formulation base. The system of active ingredient and formulation base thus must be adequately stable and must not tend toward, e.g., chemical reactions among the components or toward separation effects. Moreover, the following requirements are to be imposed on the formulation base:

- adequate homogeneous dispersion of the active ingredient on the surface of the skin
- adequate moisture in the upper skin layers
- improvement in blood supply to the upper skin layers
- penetration of the active ingredient into the upper skin layers
- improvement in the elasticity of the skin
- release of active ingredient from the formulation base
- low oxidation sensitivity The base that is used in cosmetic preparations, moveover, has to meet the following subjective criteria: pleasant sensation after the preparation is applied to the skin, good moisturizing action, pleasant odor, subtle or stylish color effects, etc. The many commercially available cosmetic preparations can at most only partially meet the above-mentioned requirements. In particular, the skin penetration of the active ingredients and lipids used is often too low. A large number of preparations are, moreover, not very effective or completely ineffective.

In the broader sense, the object of this invention is therefore to prepare improved cosmetic preparations.

To achieve this general object, the vehicle systems that are known from pharmaceutical technology that are based on liposomes are proposed according to the prior art. The latter are supposed to improve especially the penetration of lipids in the epidermis. Such liposome dispersions with various inclusion compounds and phospholipids as double-layer membrane formers or so-called empty liposomes without inclusion compounds are described in numerous publications and have already been clinically tested. In the literature, numerous processes for the production of liposome dispersions are described, e.g., by treatment of an aqueous phospholipid dispersion with ultrasound, dispersion of phospholipids with surfactants in the aqueous phase, dissolution of phospholipids in organic solvents, removal of the solvent by freeze-drying and dispersion of the residue in the aqueous phase, infusion methods, or reverse phase evaporation. Many production processes are disadvantageous since only a fraction of the amount of phospholipids used forms liposomes and these liposomes also contain only a fraction of the inclusion compounds. For cosmetic purposes, therefore, "empty" liposomes without inclusion compounds are produced almost exclusively. In the known production processes, mixed micelles, gel structures, and double-layer aggregates of undefinable sizes can additionally be formed. Known are also stability problems, greatly varying size distribution of the liposomes, inadequate reproducibility of the processes themselves, high residual amounts of organic solvents, etc.

To achieve the object, therefore, other finely dispersed systems based on lipid mixtures can be used.

Known from document WO 96/37192 are pharmaceutical or cosmetic compositions that, in combination with a sphingolipid or glycolipid (ceramide), contain the following: a partial fatty acid ester of polyoxyethylene sorbitan, a phospholipid, a triglyceride, and a therapeutic active ingredient, in water (and optionally alcohol) as a carrier liquid.

It has been found, surprisingly enough, that also insoluble in water, liquid to highly-viscous, oily or in any case oil-soluble active ingredients, e.g., fat-soluble vitamins, therapeutic oils or substances for protection from light, can be solubilized in the form of a dispersion of nanoparticles (nanodispersion) with a similar adjuvant mixture such as a partial fatty acid ester of polyoxyethylene sorbitan phospholipid, and ethanol. In the more narrow sense, the object of the invention is to produce aqueous forms of administration that are suitable for oil-soluble cosmetic active ingredients with low water-solubility.

It has been found, surprisingly enough, that an especially homogeneous finely dispersed system based on nanoparticles (nanodispersion) can be produced by dissolving an oil-soluble active ingredient that is suitable for skin cosmetics in the above-described adjuvant mixture and dispersing in water the solution that is obtained.

The subject of this invention is a cosmetic preparation in the form of a nanodispersion that contains
- a) at least one oil-soluble active ingredient that is suitable for skin cosmetics,
- b) a partial fatty acid ester of polyoxyethylene sorbitan,
- c) at least one basically pure phospholipid of formula

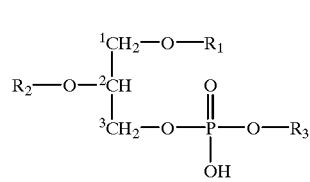

(I)

in which R. means $C_{10-20}$ acyl, $R_2$ means hydrogen or $C_{10-20}$ acyl, $R_3$ means hydrogen, 2-trimethylamino-1-ethyl, 2-amino-1-ethyl, $C_{1-4}$ alkyl $C_{2-5}$ alkyl substituted by carboxy $C_{2-5}$ alkyl substituted by hydroxy, $C_{2-5}$ alkyl substituted by carboxy and hydroxy or $C_{2-5}$ alkyl substituted by carboxy and amino, the inositol group or the glyceryl group, or salts of these compounds.
- d) ethanol in the purity that is necessary for dermal applications,
- e) water as a carrier liquid in the purity that is necessary for dermal application; and optionally
- f) other additives that are suitable for cosmetic preparations.

A cosmetic composition with components a), b), c), d) and e) is distinguished by advantageous phase properties of the solubilized ingredients. Thus, while having opalescence and transparency in back lighting, only an extremely slight milky cloudiness hints that the dispersion has physical differences from the ideal state of a true molecular solution. Electron-microscopic images show that a population of greater than 98% of the solubilized ingredient is present in a Gaussian dispersion as a suspension of particles (nanoparticles) with a particle size of less than about 60 nm (nanodispersion). These differences relative to a true solution can be tolerated, however, owing to the especially good homogeneity properties of the dispersion, which are demonstrated by, for example, a surprisingly long shelf life, e.g., no separation after storage for several months at temperatures up to room temperature (by extrapolation of the expected stability for more than two years).

The cosmetic composition is also very well suited for use in a metering spray as a clean, practical form of application. In the metering spray, preferably a pump metering spray without propellant, the composition remains sterile.

A preferred embodiment of the invention relates to
 a) at least one active ingredient that is suitable for skin cosmetics from the group of oil-soluble vitamins that can be applied dermally, cosmetic or therapeutic oils and/or oil-soluble sunblocks,
 b) a partial fatty acid ester of polyoxyethylene sorbitan;
 c) at least one basically pure phospholipid of formula (I),
 d) ethanol, in the purity that is necessary for dermal applications,
 e) water as a carrier liquid in the purity that is necessary for dermal application; and optionally
 f) other additives that are suitable for cosmetic preparations.

An especially preferred embodiment of the invention relatesto
 a) at least one of the active ingredients that are suitable for skin cosmetics from the group of oil-soluble vitamins that can be applied dermally, cosmetic or therapeutic oils and/or oil-soluble sunblocks such as UV-A and UV-B absorbers,
 b) polyoxyethylene-(20)-sorbitan monooleate;
 c) purified lecithin from soybeans;
 d) ethanol in the purity that is necessary for dermal applications;
 e) water as a carrier liquid in the purity that is necessary for dermal application; and optionally
 f) other additives that are suitable for cosmetic preparations.

The terms and designations used above and below are defined within the framework of the description of this invention as follows:

The term cosmetic preparation comprises preparations that can be applied dermally or topically, such as creams, e.g., grease creams or dry creams, o/w-, w/o-, w/o/w- emulsions, lotions, gels, sprays, ointments, pastes, and foams.

The term nanodispersion refers to a finely dispersed system of a suspended lipophilic phase in an aqueous or aqueous-alcoholic phase. Nanodispersions can be detected from, e.g., electron-microscopic images. Thus, populations of suspended particles (nanoparticles) with a particle size of less than about 80 nm (nanodispersion), preferably less than 50 nm, are present.

Component a) An active ingredient that is suitable for skin cosmetics, an active ingredient composition or an active ingredient extract is an ingredient or a mixture of ingredients that is selected from the group of oil-soluble vitamins or placenta extracts that can be applied to the skin and have a vitamin base, enzymes, allantoin, azulene, extracts of plants and plant buds, royal jelly extracts, thickened fruit and vegetable juices, cosmetic and therapeutic oils, as well as oil-soluble sunblocks, and is approved for dermal or topical administration.

Oily or oil-soluble vitamins that can be applied dermally are, e.g., vitamin A (retinol in the form of free acid or its derivatives), panthenol, pantothenic acid, folic acid and combinations thereof), vitamin E (tocopherol), F: essential fatty acids.

Placenta extracts with a vitamin base are active ingredient compositions mainly with vitamins A, C, E, $B_2$, $B_{12}$, folic acid, and biotin, amino acids and enzymes, as well as compounds of the trace elements magnesium, silicon, phosphorus, calcium, manganese, iron, or copper.

Cosmetic or therapeutic oils that can be applied dermally are neutral oils such as Miglyol 812, apricot kernel oil, avocado oil, babassu oil, cottonseed oil, borage oil, thistle oil, peanut oil, gamma-oryzanol, rose hip kernel oil, hempseed oil, hazelnut oil, currant seed oil, jojoba oil, cherry pit oil, salmon oil, linseed oil, corn oil, macadamia nut oil, almond oil, evening primrose oil, mink oil, olive oil, pecan nut oil, peach-kernel oil, pistachio kernel oil, rapeseed oil, rice kernel oil, castor oil, safflower oil, sesame oil, soybean oil, sunflower seed oil, grape-seed oil, wheat germ oil.

Suitable sunblocks are filtering substances ("sunscreens") that can absorb UV radiation from sunlight and convert it into heat. Depending on the desired action, the following sunblocks are preferred: sunblocks that selectively absorb high-energy UV-radiation in the range of about 280–315 nm (UV-B absorbers) that produce sunburn and transmit the longer-wave range of about 315–400 nm (UV-A range), as well as sunblocks that absorb only the longer-wave radiation in the UV-A range of 315–400 nm (UV-A absorbers).

Suitable sunblocks are selected preferably from the group of anthranilic acid derivatives, salicylic acid derivatives, cinnamic acid ester derivatives, coumarin derivatives, o-aminobenzoic acid derivatives, benzophenone, and benzylidene camphor.

Specific UV-B absorber, are, e.g., 4-aminobenzoic acid, 2-ethylhexyl-4-methoxy-cinnamate, 2-ethylhexylsalicylate, or UV-A absorbers, e.g., benzophenone-4, benzophenone-3, or benzophenone-10. Suitable sunblocks are described in Pflegekosmetik: Ein Leitfaden [Cosmetics: A Manual], W. Raab, U. Kindl, Govi-Verlage [Govi Publishing House], D-Frankfurt 1991 and in Ullmann's Encyclopedia of Industrial Chemistry, VCH Publishers, Fifth Complete Revised Edition, Volume A 24, Entry Skin Cosmetics.

Component a) is present in the cosmetic composition that is defined above in a preferred dosage of 0.1 to 20% by weight, relative to the total weight of the formulation.

Component b)—partial fatty acid ester of polyoxyethylene sorbitan—preferably consists of a basically pure ester or the mixture of various esters of sorbitan, in which the structure of the fatty acid groups and the length of the polyoxyethylene chain vary. Sorbitan is preferably etherified by three hydrophilic polyoxyethylene chains and esterified by a hydrophobic fatty acid group. Sorbitan can, however, also be etherified only by one or two hydrophilic polyoxyethylene chains and esterified accordingly by three or two hydrophobic fatty acid groups. The sorbitan base is generally substituted by at least one to at most three hydrophilic groups and accordingly by at most three and at least one hydrophobic group, whereby the term hydrophilic group comprises the polyoxyethylene chains and the term hydrophobic group comprises fatty acid groups.

The polyoxyethylene chain is straight-chain and has preferably 4–10, and especially 4–8, ethylene oxide units. The ester groups at the sorbitan base are derived from a saturated or unsaturated, straight-chain carboxylic acid and an even number of 8–20 C atoms. The ester group that is derived from this carboxylic acid is preferably straight-chain with 12, 14, 16 and 18 C atoms, e.g., n-dodecanoyl, n-tetradecanoyl, n-hexadecanoyl or n-octadecanoyl. The ester group that is derived from an unsaturated carboxylic acid with an even number of 8–20 C atoms is preferably straight-chain with 12, 14, 16 and 18 C atoms, e.g., oleoyl. The above-mentioned esters of sorbitan comply with the information given in the British Pharmacopeia (special monograph) or Ph. Helv. VII. Especially the product descriptions that are published by the above-mentioned manufacturers comply with information on specification sheets for the products in question, especially specifications such as shape, color, HLB value, viscosity, climbing melting point, and solubility.

Suitable partial fatty acid esters of polyoxyethylene sorbitan are commercially available under the word mark Tween$^{(R)}$ from the ICI company and the chemical designations polyoxyethylene-(20 or 4)-sorbitan monolaurate (TWEEN 20 and 21), polyoxyethylene-(20)-sorbitan monopalmitate or -monostearate (TWEEN 40 and 60), polyoxyethylene-(4 or 20)-sorbitan monostearate or -tristearate (TWEEN 61 and 65), polyoxyethylene-(20 or 5)-sorbitan monooleate (TWEEN 80 or 81) or polyoxyethylene-(20)-sorbitan trioleate (TWEEN 85) are known.

In an especially preferred embodiment of the invention, polyoxyethylene-(20)-sorbitan monooleate (TWEEN 80) is used as component b).

Component b) is present in the cosmetic composition at a proportion (relative to the total weight of the formulation) of about 0.1% to about 5%, preferably 0.5% to 3%.

Component c)—phospholipid of formula I. The nomenclature of phospholipid (I) and the numbering of the C atoms are based on the recommendations (sn-nomenclature, stereospecific numbering) provided in Eur. J. of Biochem. 79, 11–21 (1977) "Nomenclature of Lipids" by the IUPAC-IUB Commission on Biochemical Nomenclature (CBN).

$R_1$ and $R_2$ with the meaning of $C_{10-20}$ acyl are preferably straight-chain $C_{10-20}$ alkanoyl with an even number of C atoms and straight-chain $C_{10-20}$ alkenoyl with a double bond and an even number of C atoms.

Straight-chain $C_{10-20}$ alkanoyl $R_1$ and $R_2$ with an even number of C atoms are, for example, n-dodecanoyl, n-tetradecanoyl, n-hexadecanoyl or n-octadecanoyl.

Straight-chain $C_{10-20}$ alkenoyl $R_1$ and $R_2$ with a double bond and an even number of C atoms are, for example, 6-cis- or 6-trans-, 9-cis- or 9-trans-dodecenoyl, -tetradecenoyol, -hexadecenoyl, octadecenoyl or -icosenoyl, especially 9-cis-octadecenoyl (oloeyl), also 9,12-cis-octadecadienoyl or 9,12,1 5-cis-octadecatrienoyl.

A phospholipid (I) in which $R_3$ means 2-trimethylamino-1-ethyl is commonly referred to as lecithin, and a phospholipid (I) in which $R_3$ means 2-amino-1-ethyl is commonly referred to as kephalin. For example, naturally occurring kephalin or lecithin, e.g., kephalin or lecithin from soybeans or hens' eggs, with different or identical acyl groups $R_1$ and $R_2$ or mixtures thereof, are suitable.

Phospholipid (I) can also be of synthetic origin, however. Phospholipids that have a uniform composition relative to $R_1$ and $R_2$ are defined by the term synthetic phospholipid. Such synthetic phospholipids are preferably the lecithins and kephalins that are defined above; their acyl groups $R_1$ and $R_2$ have a defined structure and are derived from a defined fatty acid with a degree of purity of greater than about 95%. $R_1$ and $R_2$ can be the same or different and unsaturated or saturated. Preferably, $R_1$ is saturated, e.g., n-hexadecanoyl, and $R_2$ is unsaturated, e.g., $^9$-cis-octadecenoyl (oleoyl).

The term "naturally occurring" phospholipid (I) defines phospholipids that do not have a uniform composition in terms of $R_1$ and $R_2$. Such natural phospholipids are also lecithins and kephalins, their acyl groups $R_1$ and $R_2$ cannot be defined structurally and are derived from naturally occurring fatty acid mixtures.

The requirement "basically pure" phospholipid (I) defines a degree of purity of greater than 90% (by weight), preferably more than 95%, of phospholipid (I), which can be detected by suitable determination methods, e.g., by paper chromatography, with thin-layer chromatography, with HPLC or an enzymatic color test.

In a phospholipid (I), $R_3$ with the meaning of $C_{1-4}$ alkyl is, for example, methyl or ethyl. The meaning of methyl is preferred.

$R_3$ with the meanings $C_{1-5}$ alkyl substituted by carboxy, $C_{2-5}$ alkyl substituted by hydroxy or $C_{2-5}$ alkyl substituted by carboxy or hydroxy are, for example, 2-hydroxyethyl, 2,3-dihydroxy-n-propyl, carboxymethyl, 1- or 2-carboxyethyl, dicarboxymethyl, 2-carboxy-2-hydroxyethyl or 3-carboxy-2,3-dihydroxy-n-propyl.

$R^3$ with the meaning $C_{2-5}$ alkyl is substituted by carboxy and amino, e.g., 3-amino-3-carboxy-n-propyl or 2-amino-2-carboxy-n-propyl, preferably 2-amino-2-carboxyethyl. Phospholipids (I) with these groups can be present in the form of a salt, e.g., as a sodium or potassium salt.

Phospholipids (I) in which $R_3$ means the inositol group or the glyceryl group are known under the designations phosphatidylinositol and phosphatidylglycerol.

For acyl radicals in phospholipids (I), the designations that are indicated in parentheses are also commonly used:

9-cis-dodecenoyl (lauroleoyl), 9-cis-tetradecenoyl (myristoleoyl), 9-cis-hexadecenoyl (palmitoleoyl), 6-cis-octadecenoyl (petroseloyl), 6-trans-octadecenoyl (petroselaidoyl), 9-cis -octadecenoyl (oleoyl), 9-trans-octadecenoyl (elaidoyl), 9,12-cis-octadecadienoyl (linoleoyl), 9,12,15-cis-octadecatrienoyl (linolenoyl), 11-cis-octadecenoyl (vaccenoyl), 9-cis-icosenoyl (gadoloeoyl), 5,8,11,14-cis-eicosatetraenoyl (arachidonoyl), n-dodecanoyl (lauroyl), n-tetradecanoyl (myristoyl), n-hexadecanoyl (palmitoyl), n-octadecanoyl (stearoyl), n-icosanoyl (arachidoyl), n-docosanoyl (behenoyl), n-tetracosanoyl (lignoceroyl).

A salt of phospholipid (I) is preferably pharmaceutically acceptable. Salts are defined by the existence of salt-forming groups in substituent $R_3$, as well as by the free hydroxy group on phosphorus. The formation of internal salts is also possible. Preferred are alkali metal salts, especially sodium salts.

Component c) is added at a preferred concentration of about 0.1 to 5% by weight, preferably 0.5 to 3% by weight, relative to the total weight of the formulation. In an especially preferred embodiment, purified lecithin from soybeans of grade LIPOID S 100 is used.

Component d) preferably consists of absolute ethanol.

Component e)—water in the purity that is necessary for dermal application—is germ-free and, if necessary, pyrogen-free according to the applicable instructions of the National Pharmacopeia.

Component f)—adjuvants suitable for a dermal form of administration—is contained as a facultative ingredient. Such adjuvants are contained in o/w-, w/o-, w/o/w- emulsions, creams, ointments, gels, lotions, pastes, spray foams, sprays, aerosols, tinctures, or lotions.

Suitable are especially emulsifiers, fatty acid salts, e.g., sodium stearate, emulsifying mixtures made of fatty acids and their salts, e.g., the mixture of stearic acid and sodium stearate, ethoxylated fatty alcohols, e.g., polyoxyethylene (20)-cetyl-stearyl ether, hydrogenated ethoxylated castor oil, e.g., polyoxyethylene(7)-hydroxygenated castor oil, fatlike emulsifiers, e.g., wool wax, wool wax alcohols, higher fatty alcohols, or partial glycerine esters or partial sorbitan esters such as glycerine monostearate or sorbitan monooleate, orthophosphoric acid ester, e.g., cetyl phosphate, or surfactants with a silicon base, e.g., dimethiconpolyol. Lipophilic components, silicon oils or silicon waxes, fatty acid esters such as cetyl palmitate, isostearyl isostearate, isopropyl palmitate or isopropyl myristate, mineral oil, vaseline, natural wax or Guerbet alcohols, also preservatives, e.g., benzalkonium chloride, phenoxy-ethanol, also benzoic acid or its salts, 4-hydroxy-benzoic acid ester (pHB ester), phenols, e.g., tert-butyl-4-methoxy- or di-tert-butyl-4-methylphenol, benzyl alcohol, 4-chlorobenzyl or 2,4-dichlorobenzyl alcohol, 2-phenylethanol, chlorohexidine diacetate or chlorohexidine digluconate, thiabendazole, cetyl triammonium bromide, cetyl-pyridininum bromide, phenododecinium bromide or sorbic acid, stabilizers that prevent separation (demulsification), e.g., tragacanth gum, starch, dextrins, pectins, alginates, cellulose esters, egg whites or polyvinyl alcohol, regulators of the moisture of the skin, e.g., amino acids, such as alanine, argininine, glutamic acid, glycine, histidine, serine or 2-pyrrolidone-5-carboxylic acid or sodium lactate, collagen-hydrolysates, sugar (pentoses) or reaction products of D-glucose and L-glutamic acid, anitioxidants, e.g., ascorbic acid, cysteine, sulfites, e.g., sodium bisulfite, thioglycol or glutathione, essential oils for improving odor, e.g., menthol, orange, bitter orange, mandarin orange or citric oil, solvents or anti-evaporation agents, e.g., poly alcohols, e.g., propylene glycol, polyethylene glycol or glycerine, also pigments for improving color hue, e.g., talc, zinc oxide, kaolin, titanium dioxide, iron oxide, chromium oxide, manganese violet, ultramarine, or dyes with mica effects, e.g., mica.

The adjuvant content of component f) can vary within wide limits and depends on the type and the aesthetic nature of the desired form of preparation. As a general upper limit, a maximum content of about 20% by weight is considered.

To improve the skin penetration of the ingredients, so-called penetrating agents (flux enhancers) can be added which improve the penetration in upper skin layers. Suitable penetrating agents are, e.g., amides, e.g., N,N-dimethyllauroyl amide, 1-n-dodecylazacyclo-heptan-2-one (Azone$^{(R)}$, Nelson), N-methyl-2-pyrrolidone, urea or isopropyl myristate.

An object of the invention is also the process for the production of the cosmetic composition according to claim 1, which is characterized in that component c)—phospholipid —is dissolved in component d)—ethanol—, then component b)—partial fatty acid ester of polyoxyethylene sorbitan—as well as component a)—active ingredient—are added, and the mixture is stirred at room temperature or at an elevated temperature.

According to this process, an especially homogeneous dispersion with nanoparticles of lipophilic ingredient a) that can be applied dermally is produced.

The nanodispersion is obtained by adding the lipophilic phase ("oil phase") that consists of the ingredients of component a), as well as components b), c), d) and optionally lipophilic adjuvants—component f)—to the aqueous phase—component e), which optionally contains other hydrophilic adjuvants—component f). The mixture is mixed for two to three hours with a magnetic stirrer or a static mixer. The mixing process is carried out preferably at room temperature or with slight warming of up to 45° C.

The dispersion that is thus obtained can be defined as a dispersion of colloid nanoparticles or, in simplified terms, as a nanodispersion. Based on laser-light scatter measurements and electron microscope pictures, the colloid particles that are present in the dispersion can be distinguished from other entities such as liquid crystals, micelles, reverse micelles, or liposomes. For the statistical majority of more than 95%, preferably more than 99%, a mean particle size of less than 80 nm is characteristic.

To characterize the available nanodispersions, methods known in the art are suitable, e.g., optical evaluation: weak to strong opalescence of the preparation is readily detectable (indication of a mean particle size of less than 50 nm), laser-light scatter (determination of particle size and homogeneity); electron microscopy (freeze-break- and negative contrast techniques).

The following examples illustrate the invention; percentages are given in percent by weight; relevant physical-chemical parameters, such as nanoparticle sizes and nanoparticle dispersion (laser-light scatter measurements in the nm range), (particle counter according to USP in the $\mu$m range), viscosity and active ingredient content of the formulations in connection with the examples are summarized in a table.

EXAMPLE 1

Formulation for a vitamin E nanodispersion 94.701% aqua purificata [purified water]
2.000% tocopheroli acetas (alpha) Ph. Eur. III
1.350% Polysorbatum 80 Ph. Eur. III
1.000% lipoid S 100
0.650% ethanolum absolutum [absolute ethanol]
0.272% natrii dihdrogenophosphas dihydricus Ph. Eur. III
0.027% dinatrii phosphas dihydricus Ph. Eur. IIII Lipoid S 100 is dissolved in ethanol, Polysorbatum 80 and Tocopheroliacetas are added, this oil phase is added to the aqueous phase—which contains both buffer salts—, and it is stirred for two to three hours (200–300 rpm) at room temperature until the mixture is transparent and weakly opalescent.

EXAMPLE 2

Formulation for a vitamin A nanodispersion 96.129% aqua purificata
1.497% Polysorbatum 80 Ph. Eur. III
1.000% lipoid S 100
0.650% ethanolum absolutum
0.325% vitamin A palmitate 1.7M IU/g (Toc)
0.272% natrii dihydrogenophosphas dihydricus Ph. Eur. III
0.100% tocopheroli acetas (alpha) Ph. Eur. III
0.027% dinatrii phosphas dihydricus Ph. Eur. III The procedure is carried out in a way that is analogous to Example 1.

EXAMPLE 3

Formulation for a macadamia nut oil nanodispersion 92.560% aqua purificata
2.133% refined macadamia nut oil 1.800% Polysorbatum 80 Ph. Eur. III
1.333% lipoid S 100
0.867% ethanolum absolutum
0.533% tocopheroli acetas (alpha) Ph. Eur. III
0.500% phenoxyethanol
0.247% kalii dihydrogenophosphas DAB10
0.027% dinatrii phosphas dihydricus Ph. Eur. III
The procedure is carried out in a way that is analogous to Example 1.

EXAMPLE 4

Formulation of a currant seed oil nanodispersion 94.226% aqua purificata
2.000% refined currant seed oil
1.350% Polysorbatum 80 Ph. Eur. III
1.000% lipoid S 100
0.650% ethanolum absolutum
0.500% phenoxyethanol
0.247% kalii dihydrogenophosphas DAB10
0.027% dinatrii phosphas dihydricus Ph. Eur. III
The procedure is carried out in a way that is analogous to Example 1.

EXAMPLE 5

Formulation for an almond oil nanodispersion 94.226% aqua purificata
2.000% refined almond oil Ph. Eur. III
1.350% Polysorbatum 80 Ph. Eur. III
1.000% lipoid S 100
0.650% ethanolum absolutum
0.500% phenoxyethanol
0.247% kalii dihydrogenophosphas DAB10
0.027% dinatrii phosphas dihydricus Ph. Eur. E
The procedure is carried out in a way that is analogous to Example 1.

EXAMPLE 6

Formulation for a Parsol MCX nanodispersion 95.000% aqua purificata
2.500% Parsol MCX
0.944% lipoid S 100
0.723% ethanolum absolutum
0.585% Polysorbatum 80 Ph. Eur. III
0.248% miglyol 812 neutral oil
The procedure is carried out in a way that is analogous to Example 1.

EXAMPLE 7

Formulation for a dexpanthenol 5% nanodispersion metering spray formulation 88.315% aqua purificata
6.667% D-panthenol 75L USP23
1.434% miglyol 812 neutral oil DAB10
1.413% Polysorbatum 80 Ph. Eur. III 1.717% lipoid S 100
0.600% phenoxyethanol
0.591% ethanolum absolutum
0.237% kalii dihydrogenophosphas DAB10
0.026% dinatrii phosphas dihydricus Ph. Eur. III
The procedure is carried out in a way that is analogous to Example 1, whereby the nanodispersion that is sterilized by filtration is produced in a pump metering spray with 30 ml of contents.

The physical-chemical parameters of the cosmetic formulations are listed in the table below:

| Example | Batch No. and Size [kg] | Laser-light Scatter[1] nanoparticle size ± S.D. [mm] | Viscosity [mPa*s] |
|---|---|---|---|
| 1 | 503.001 5.0 | 30.5 ± 4.4 | 1.4 |
| 2 | 305.002 5.0 | 21.5 ± 4.4 | 1.2 |
| 3 | 307.002 5.0 | 24.5 ± 5.7 | 1.3 |
| 4 | 310.001 5.0 | 19.5 ± 2.0 | 1.3 |
| 5 | 312.001 5.0 | 35.7 ± 6.0 | 1.3 |
| 6 | 990.023 0.5 | 71.4 ± 13.8 | 1.2 |
| 7 | 905.012 3.6 | 21.2 ± 4.2 | 1.6 |

[1]Nicomp 370 Simicron Particle Sizer; Nicomp Distribution Analysis Number Weighting

We claim:
1. Cosmetic preparation in the form of a nanodispersion, said preparation comprising
   a) at least one oil-soluble active ingredient that is suitable for skin cosmetics; in a cosmetically effective amount
   b) 0.1% to 5% of a partial fatty acid ester of polyoxyethylene sorbitan;
   c) 0.1% to 5% of at least one basically pure phospholipid of formula

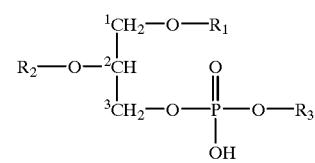

1)

in which $R_1$ means $C_{10-20}$ acyl, $R_2$ means hydrogen or $C_{10-20}$ acyl, $R_3$ means hydrogen, 2-trimethylamino-1-ethyl, 2-amino-1-ethyl, $C_{1-4}$ alkyl, $C_{1-5}$ alkyl substituted by carboxy, $C_{2-5}$ alkyl substituted by hydroxy, $C_{2-5}$ alkyl substituted by carboxy and hydroxy or $C_{2-5}$ alkyl substituted by carboxy and amino, the inositol group or the glyceryl group, or salts of these compounds,
   d) ethanol in the purity that is necessary for dermal applications,
   e) water as a carrier liquid in the purity that is necessary for dermal application.
2. Cosmetic preparation according to claim 1, characterized in that component (a) is present in the preparation at a dosage of 0.1 to 20% by weight, relative to the total weight of the preparation.
3. Cosmetic preparation according to one of claims 1 to 2, wherein the active ingredient that is suitable for skin cosmetics is selected from the group that consists of oil-soluble vitamins, cosmetic or therapeutic oils, and oil-soluble sunblocks that can be applied dermally.

4. Cosmetic preparation according to claim 3, wherein the active ingredient that is suitable for skin cosmetics is selected from the group that consists of oil-soluble vitamins, cosmetic or therapeutic oils, and oil-soluble sunblocks such as UV-A and UV-B absorbers that can be applied dermally.

5. Cosmetic preparation according to one of claims 1 to 4, wherein the partial fatty acid esters of polyoxyethylene sorbitan (b) is polyoxyethylene-(20)-sorbitan monooleate.

6. Cosmetic preparation according to one of claims 1 to 5, wherein phospholipid (c) is purified lecithin from soybeans.

7. Cosmetic preparation according to one of claims 1 to 6, wherein, in addition to the indicated substances, it contains other additives that are suitable for cosmetic preparations.

8. Process for the production of a cosmetic preparation according to one of claim 1 to 4, comprising steps of dissolving component (c)—phospholipid—in component (d)—ethanol, then adding component (b)—partial fatty acid esters of polyoxyethylene sorbitan—and component (a)—active ingredient—to form an oil phase, then adding said oil phase to component (e)—the aqueous phase, and then stirring the mixture, thereby to form a spontaneous nanodispersion.

9. Cosmetic preparation in the form of a nanodispersion, produced by the process according to claim 8.

* * * * *